(12) United States Patent
Baudenbacher et al.

(10) Patent No.: US 10,179,083 B2
(45) Date of Patent: Jan. 15, 2019

(54) COMPRESSION DEVICE, SYSTEM, AND METHOD FOR DECREASING ABDOMINAL VENOUS POOLING

(71) Applicant: Vanderbilt University, Nashville, TN (US)

(72) Inventors: Franz Baudenbacher, Franklin, TN (US); Italo Biaggioni, Nashville, TN (US); Rene Harder, Nashville, TN (US); Andre Diedrich, Nashville, TN (US); Luis Okamoto, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 572 days.

(21) Appl. No.: 14/439,824

(22) PCT Filed: Nov. 4, 2013

(86) PCT No.: PCT/US2013/068270
§ 371 (c)(1),
(2) Date: Apr. 30, 2015

(87) PCT Pub. No.: WO2014/071292
PCT Pub. Date: May 8, 2014

(65) Prior Publication Data
US 2015/0313608 A1    Nov. 5, 2015

Related U.S. Application Data

(60) Provisional application No. 61/721,781, filed on Nov. 2, 2012.

(51) Int. Cl.
*A61H 11/00* (2006.01)
*A61H 9/00* (2006.01)
(Continued)

(52) U.S. Cl.
CPC .......... *A61H 11/00* (2013.01); *A61B 17/1355* (2013.01); *A61F 5/34* (2013.01);
(Continued)

(58) Field of Classification Search
CPC ........ A61H 9/00; A61H 9/005; A61H 9/0078; A61H 9/0085; A61H 9/0092; A61H 11/00;
(Continued)

(56) References Cited

U.S. PATENT DOCUMENTS 2,869,537 A * 1/1959 Chu ...................... A61H 9/0078
482/112
6,010,470 A * 1/2000 Albery ................. A61H 9/0092
601/149
(Continued)

FOREIGN PATENT DOCUMENTS

EP         2436349         4/2012
WO      2007136784      11/2007
(Continued)

OTHER PUBLICATIONS

ISA for corresponding International Pat. Appl. No. PCT/US2013/068270, dated May 2, 2014, 3 pages.

*Primary Examiner* — Valerie L Woodward
(74) *Attorney, Agent, or Firm* — Tarolli, Sundheim, Covell & Tummino LLP

(57) ABSTRACT

A compression device can include an adjustable belt, an inflation bladder, and a control module. The adjustable belt can be sized to fit circumferentially around a subject's abdomen. The inflatable bladder and the control module can be secured to the belt. The control module can include a housing that encloses at least one of a pump, a pressure relief valve, and a controller. The pump and the pressure relief valve can be in fluid communication with the bladder. The pump can be configured to inflate the bladder to a pre-
(Continued)

determined pressure and apply a compressive pressure to the subject's abdomen. The pressure relief valve can be configured to decrease the pressure within the bladder. The controller can be configured to automatically adjust the compressive pressure in response to a change in the subject's posture. The controller can be in electrical communication with the pump and the pressure relief valve.

19 Claims, 11 Drawing Sheets

(51) Int. Cl.
    *A61B 17/135*     (2006.01)
    *A61F 5/34*     (2006.01)
    *A61B 17/00*     (2006.01)

(52) U.S. Cl.
    CPC .. *A61H 9/0078* (2013.01); *A61B 2017/00221* (2013.01); *A61H 2011/005* (2013.01)

(58) Field of Classification Search
    CPC ...... A61H 11/005; A61H 31/00; A61H 31/02; A61H 31/025; A61B 17/1355
    See application file for complete search history.

(56) References Cited

U.S. PATENT DOCUMENTS

| | | | |
|---|---|---|---|
| 2007/0088235 A1* | 4/2007 | Tseng | A61H 9/0078 601/151 |
| 2011/0093003 A1* | 4/2011 | Lee | A61B 17/1355 606/201 |
| 2012/0065561 A1* | 3/2012 | Ballas | A61H 9/0021 601/152 |
| 2012/0078145 A1* | 3/2012 | Malhi | A61H 9/0092 601/149 |
| 2014/0094726 A1* | 4/2014 | Malhi | A61H 9/00 601/152 |
| 2016/0374886 A1* | 12/2016 | Wyatt | A61N 1/36014 601/18 |

FOREIGN PATENT DOCUMENTS

| | | |
|---|---|---|
| WO | 2009055162 | 4/2009 |
| WO | 2012135613 | 10/2012 |

* cited by examiner

COMPRESSION DEVICE, SYSTEM, AND METHOD FOR DECREASING ABDOMINAL VENOUS POOLING

RELATED APPLICATION

This application is a U.S. National Stage under 35 USC 371 patent application, claiming priority to Serial No. PCT/US2013/068270, filed on Nov. 4, 2013; which claims the benefit of U.S. Provisional Patent Application Ser. No. 61/721,781, filed Nov. 2, 2012, the entirety of which is hereby incorporated by reference for all purposes.

TECHNICAL FIELD

The present disclosure relates generally to medical devices and methods and, more particularly, to compression devices, systems, and methods for decreasing abdominal venous pooling in a subject.

BACKGROUND

Orthostatic hypotension (OH) is the most disabling manifestation of autonomic failure and many other medical conditions, including diabetes. Orthostatic hypotension can also be seen as a consequence of medications and even aging. For example, drugs that increase vascular resistance (e.g., midodrine) and/or plasma volume (e.g., fludrocortisone) are first-line therapy. Such drugs, however, may worsen supine hypertension and may be contraindicated in patients with significant cardiovascular disease (e.g., congestive heart failure). More importantly, these approaches to treatment do not target the main reason blood pressure (BP) falls on standing, which is gravity-related venous pooling that reduces venous return and cardiac output. Most of this venous pooling occurs in the splanchnic circulation.

Abdominal compression is a safe and effective approach to improve standing BP. Thus, it is considered the standard of care in the non-pharmacologic treatment of neurogenic OH. This recommendation, however, is based on acute studies (i.e., less than two hours). And there are no controlled trials that have proven the continued efficacy of this approach, much less patient acceptance. Indeed, evidence suggests that this approach is not effective in most patients mostly due to decreased efficacy and low compliance. The limitations with currently available devices, such as elastic abdominal binders are explained by the fact that it is difficult for patients to apply pressure at an effective compression level (e.g., 20-40 mm Hg). Not only does this reduce efficacy of currently available compression devices, but such devices are also uncomfortable to wear for prolonged periods of time if kept at effective compression levels.

SUMMARY

The present disclosure relates generally to medical devices and methods and, more particularly, to compression devices, systems, and methods for decreasing abdominal venous pooling in a subject.

One aspect of the present disclosure relates to a compression device. The compression device can comprise an adjustable belt, an inflatable bladder, and a control module. The adjustable belt can be sized to fit circumferentially around the abdomen of a subject. The inflatable bladder can be secured to the belt. The control module can be secured to the belt and include a housing that encloses one or more of a pump, at least one pressure relief valve, and a controller. The pump can be in fluid communication with the bladder. The pump can be configured to inflate the bladder to a pre-determined pressure and thereby apply a compressive pressure to the abdomen of the subject. The at least one pressure relief valve can be in fluid communication with the bladder. The at least one pressure relief valve can be configured to decrease the pressure within the bladder. The controller can be configured to automatically adjust the compressive pressure in response to a change in the posture of the subject. The controller can be in electrical communication with the pump and the at least one pressure relief valve.

Another aspect of the present disclosure relates to a system for decreasing abdominal venous pooling in a subject. The system can comprise a compression device and a handheld electronic device. The compression device can comprise an adjustable belt, an inflatable bladder, and a control module. The adjustable belt can be sized to fit circumferentially around the abdomen of a subject. The inflatable bladder can be secured to the belt. The control module can be secured to the belt and include a housing that encloses one or more of a pump, at least one pressure relief valve, and a controller. The pump can be in fluid communication with the bladder. The pump can be configured to inflate the bladder to a pre-determined pressure and thereby apply a compressive pressure to the abdomen of the subject. The at least one pressure relief valve can be in fluid communication with the bladder. The at least one pressure relief valve can be configured to decrease the pressure within the bladder. The controller can be configured to automatically adjust the compressive pressure in response to a change in the posture of the subject. The controller can be in electrical communication with the pump and the at least one pressure relief valve. The handheld electronic device can be in wireless communication with the controller.

Another aspect of the present disclosure relates to a method for decreasing abdominal venous pooling in a subject. The method can comprise automatically applying a compressive pressure to the abdomen of the subject in response to a change in the posture of the subject.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
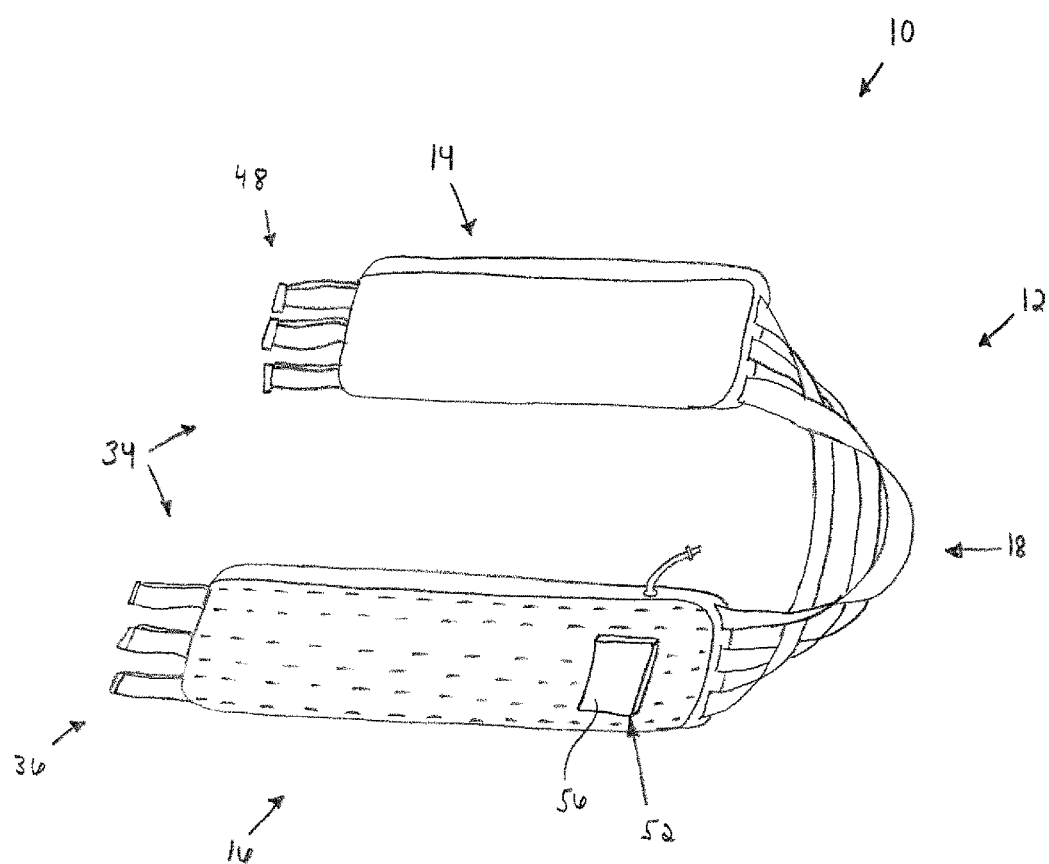
FIG. 1 is a perspective view showing a compression device for decreasing abdominal venous pooling constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y".

As used herein, phrases such as "from about X to Y" can mean "from about X to about Y".

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "subject" can be used interchangeably with the term "patient" and refer to any warm-blooded organism including, but not limited to, human beings, pigs, rats, mice, dogs, goats, sheep, horses, monkeys, apes, farm animals, livestock, rabbits, cattle, etc.

As used herein, the term "electrical communication" can refer to the ability of a generated electric field to be transferred to, or have an effect on, one or more components, structures, or elements of the present disclosure. In some instances, the generated electric field can be directly transferred to a component, structure or element (e.g., via a wire or lead). In other instances, the generated electric field can be wirelessly transferred to a component, structure or element.

As used herein, the term "orthostatic intolerance" can refer to the development of a set of characteristic symptoms while standing or sitting upright that include, but are not limited to, lightheadedness, palpitations, nausea, breathing or swallowing difficulties, headache, visual disturbances, pallor, sweating, tremors, fatigue, altered mentation and syncope. In some instances, such symptoms can be accompanied by postural tachycardia and elevated plasma norepinephrine.

Overview

The present disclosure relates generally to medical devices and methods and, more particularly, to compression devices, systems, and methods for decreasing abdominal venous pooling in a subject. As illustrated in FIG. 1, one aspect of the present disclosure can include a compression device for decreasing abdominal venous pooling in a subject. Conditions associated with orthostatic intolerance, such as orthostatic hypotension are significant medical problems caused by gravity-induced venous pooling with decreased venous return. Besides certain pharmacological agents, abdominal binders are considered to be the standard of care in the treatment of orthostatic hypotension. For several reasons, however, such devices are not optimal. For example, it is difficult for patients to apply pressure at an effective compression level (e.g., about 20-40 mm Hg). Additionally, even if an effective compression level is obtained, such devices are uncomfortable to wear for prolonged periods of time if pressure is maintained about the patient's abdomen during all forms of posture (i.e., standing, sitting and supine).

Advantageously, the present disclosure provides devices, systems, and methods that automatically adjust the effective compression level applied to a patient's abdomen to decrease venous pooling and thereby reduce orthostatic hypotension and improve upright blood pressure and orthostatic intolerance. As discussed in more detail below, the devices, systems, and methods of the present disclosure automatically adjust the amount of compression applied to a patient's abdomen based on the posture of the patient. This allows for normal physiologic changes in intra-abdominal pressure during routine activities, such as coughing, deep breathing, bending over, etc. Since effective compression is only applied when a patient is at risk of experiencing venous pooling (e.g., when standing or transitioning to standing), the present disclosure advantageously increase comfort when the patient is sitting or in a supine position. Other advantages of the present disclosure, which will be apparent to one skilled in the art, are discussed below.

Compression Devices

One aspect of the present disclosure can include a compression device. In some instances, the compression device can include an adjustable belt, an inflatable bladder secured to the belt, and a control module that is also secured to the belt. Unlike conventional abdominal binders, which are often bulky and cumbersome, the compression device of the present disclosure is shaped and dimensioned for easy application to (and removal from) a subject. For example, the compression device can have a low profile, streamlined construction that allows it to be worn under garments (e.g., a shirt or dress) without creating an unsightly or noticeable bulge around a patient's midsection. The compression device is also constructed of flexible and lightweight materials that make it ergonomical and easy to transport when not in use. The simple construction of the compression device also makes it an effective, low-cost option for effectively treating conditions associated with orthostatic intolerance, such as orthostatic hypotension.

Adjustable Belt

In another aspect, the adjustable belt of the compression device can be sized and dimensioned to fit circumferentially around the abdomen of a subject. Generally speaking, the adjustable belt can have a length, width, and thickness appropriate to facilitate snug placement of the belt around the abdomen of a subject. In one example, the length of the belt can be sufficient to wrap around an adult subject. The width of the belt should not be so wide as to constrain expansion of the thorax of the subject. In some instances, the dimensions of the belt can be tailored based on the known size (girth) of the subject. In other instances, the belt can have a one-size-fits-all configuration. In further instances, the belt can have one of a series of standard dimensions. The adjustable belt can additionally or optionally include an adjustment mechanism that enables a subject to selectively adjust the length of the belt. Non-limiting examples of adjustment mechanisms can include Velcro® straps, zippers, hook and loop fasteners, etc. The belt can be ventilated and/or padded. The belt can be made of one or combination of flexible (e.g., elastic), semi-rigid and/or rigid materials, such as nylon, neoprene, polyester, etc.

In another aspect, at least one radially inflatable bladder can be secured to the adjustable belt. In some instances, an inflatable bladder can be integrated within the belt so that the inflatable bladder is completely enveloped by the material comprising the belt. In such instances, the belt can include a pre-formed pocket configured to receive the inflatable bladder. In other instances, the inflatable bladder can be secured to an inner surface of the adjustable belt so that the inflatable bladder is disposed between the belt and the abdomen of the subject when in use. The inflatable bladder can be arranged about the belt so that inflation of the inflatable bladder imparts compressive pressure to all or only a portion of the subject's abdomen. For example, the inflatable bladder may be located about a first portion of the adjustable belt so that inflation of the bladder results in application of compressive pressure to only the ventral abdomen of the subject. The size of the inflatable bladder can be varied to accommodate a desired volume of air (e.g., about 2 L). The inflatable bladder can be made of one or a combination of materials, such as rubber, polyurethane-coated nylon fabric, etc.

FIGS. 1 and 2A-C illustrate one example of a compression device 10 according to the present disclosure. Referring to FIG. 1, the compression device 10 can include an adjustable belt 12 having a two-panel design, which provides a better custom fit for different body sizes. The belt 12 can include oppositely disposed dorsal and ventral portions (or panels) 14 and 16. The dorsal portion 14 can be configured to apply compressive pressure to only the lower back of a subject, while the ventral portion 16 can be configured to apply compressive pressure to only the abdomen of the subject. The dorsal and ventral portions 14 and 16 are joined together by one or more straps 18. The straps 18 allow better air circulation about the sides of the subject. The straps 18 also allow for better adjustment and fitting of the belt 12 to the abdomen and waist of the subject.

Figure 2A:
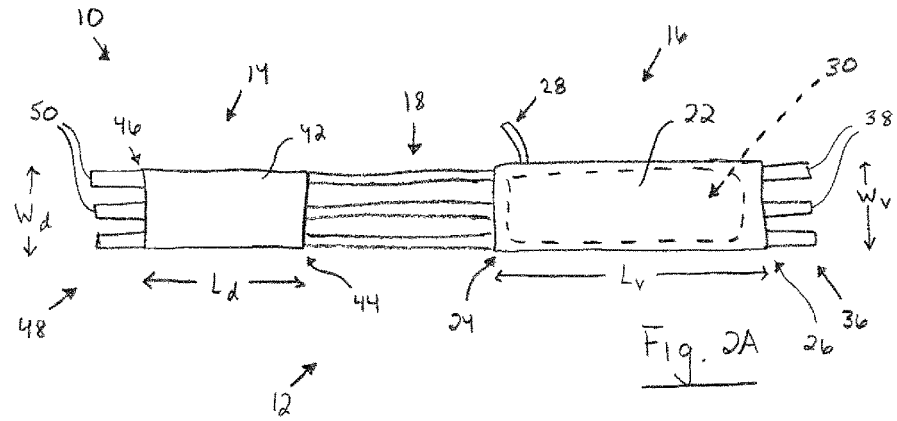
FIG. 2A is a schematic illustration showing an inner surface of the compression device in FIG. 1.
Figure 2B:
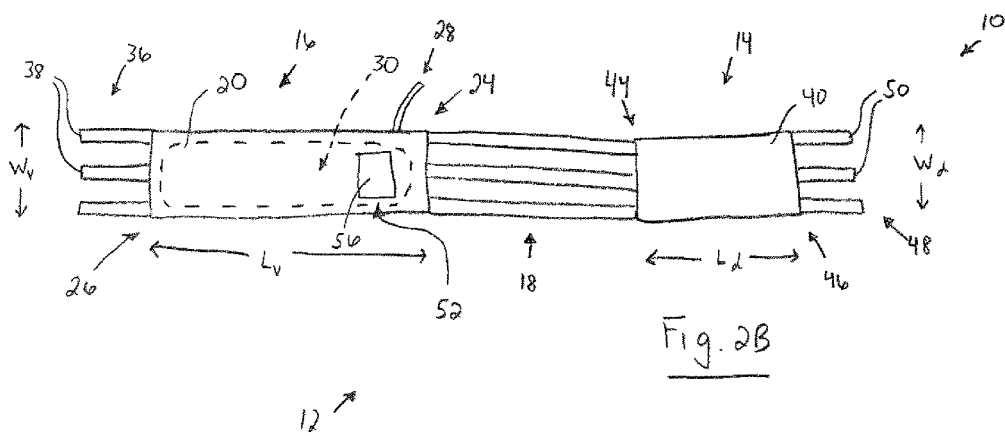
FIG. 2B is a schematic illustration showing an outer surface of the compression device in FIG. 1.
Figure 2C:
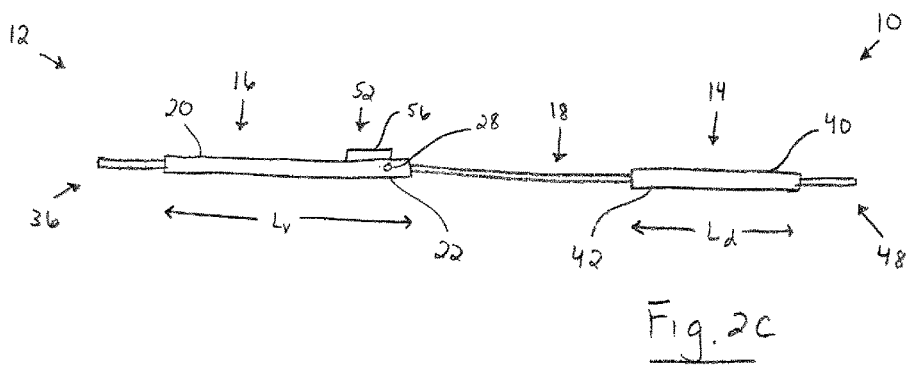
FIG. 2C is a schematic illustration showing a top view of the compression device in FIG. 1.
Figure 4:
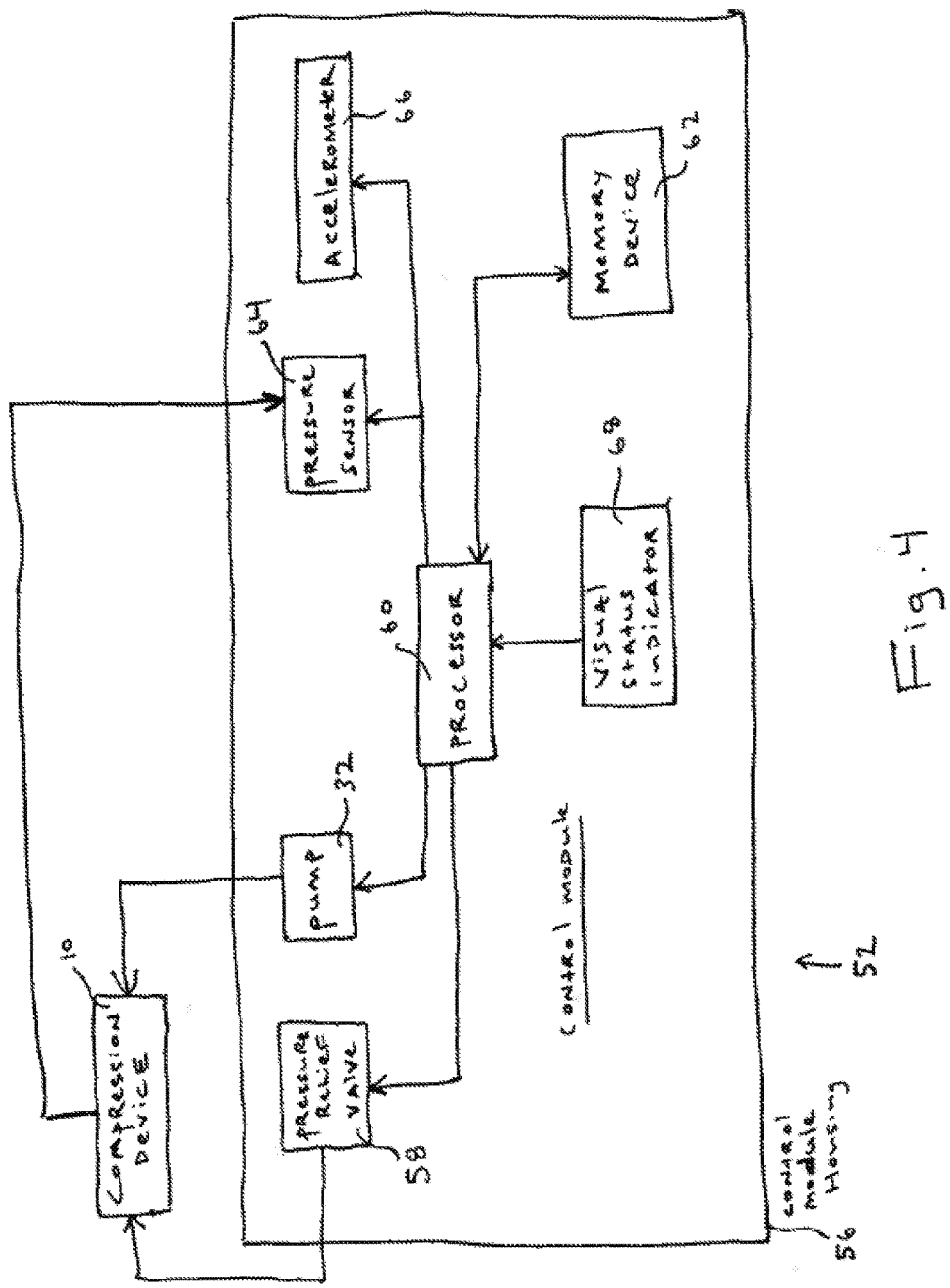
FIG. 4 is a schematic illustration showing one configuration of the control module in FIGS. 3A-B.

The ventral portion 16 (FIGS. 2A-C) has a generally rectangular configuration defined by a length $L_v$ and a width $W_v$. In one example, the length $L_v$ can be about equal to, or greater than, the width $W_v$. The ventral portion 16 can include oppositely disposed first and second major surfaces 20 and 22, as well as oppositely disposed first and second ends 24 and 26. The ventral portion 16 can also include a valve stem 28, which is in communication with an inflatable bladder 30 and/or a pump 32 (FIG. 4). The first end 24 (FIGS. 2A-C) of the ventral portion 16 is connected to the straps 18 by stitching, for example. The second end 26 of the ventral portion 16 includes an attachment mechanism 34, which is configured so that a subject can selectively connect the ventral portion to the dorsal portion 14 and thereby secure the compression device 10 about the subject's waist. As shown in FIGS. 2A-C, the attachment mechanism 34 can include three straps 36 extending from the second end 26 of the ventral portion 16. A distal end 38 of each strap 36 can include a male mating member (not shown in detail), which is configured to mate with a female mating member (not shown in detail) (e.g., via a buckle or snap-fit mechanism). It will be appreciated that the length of each strap 36 may be adjustable to accommodate various waist sizes. The attachment mechanism 34 provides not only a quick and easy means for securing and removing the compression device 10, but also a simple way to adjust the total length of the belt 12 and ensure a snug fit between the subject's waist and the compression device.

As shown in FIGS. 2A-B, a radially expandable inflatable bladder 30 can be secured to the ventral portion 16. In some instances, the inflatable bladder 30 can be disposed within the ventral portion 16. For example, the inflatable bladder 30 can be disposed within a pre-formed pocket (not shown) of the ventral portion 16 such that the material comprising the ventral portion completely envelops the inflatable bladder. In other instances, the inflatable bladder 30 can be secured to the second major surface 22 of the ventral portion 16. In such instances, an adhesive material (e.g., Velcro® strips) can be used to affix the inflatable bladder 30 to the second major surface 22. The shape and dimensions of the inflatable bladder 30 can be varied as needed to apply adequate compressive pressure to the abdomen of the subject. For instance, the inflatable bladder 30 can have a rectangular configuration with a length and width that are less than the length $L_v$ and width $W_v$ of the ventral portion 16. The inflatable bladder 30 can be made of rubber, for example, and have an inflated volume of about 2 L.

The dorsal portion 14 of the adjustable belt 12 has a generally rectangular configuration defined by a length $L_d$ and a width $W_d$. In one example, the length $L_d$ can be about equal to, or greater than, the width $W_d$. The length $L_d$ and/or width $W_d$ of the dorsal portion 14 can be less than, equal to, or greater than the length $L_v$ and/or width $W_v$ of the ventral portion 16. The dorsal portion 14 can include oppositely disposed first and second major surfaces 40 and 42, as well as oppositely disposed first and second ends 44 and 46. The first end 44 of the dorsal portion 14 can be connected to the straps 18 by stitching, for example. The second end 46 of the dorsal portion 14 can comprise the attachment mechanism 34. As shown in FIGS. 2A-C, the attachment mechanism 34 can further include three straps 48 extending from the second end 46 of the dorsal portion 14. A distal end 50 of each strap 48 can include a female mating member, which is configured to mate with the male mating member of the ventral portion 16 (e.g., via a buckle or snap-fit mechanism). It will be appreciated that the length of each strap 48 may be adjustable to accommodate various waist sizes. Advantageously, the attachment mechanism 34 is located along a lateral aspect of the subject's waist, which makes the attachment mechanism easily reachable and removes the inconvenience associated with conventional attachment mechanisms (e.g., buckles), which are often located on the back.

As shown in FIG. 1, the straps 18 can extend longitudinally across the ventral portion 16. In some instances, each of the straps can extend through a separate channel (not shown) that is embedded within the ventral portion. In other instances, each of the straps can extend across the first major surface of the ventral portion. In such instances, each of the straps can extend through one or more loops (not shown) that hold and maintain the position of each strap while also allowing each strap to slide therethrough. The presence of the straps across the ventral portion prevents the ventral portion, and in particular the first major surface, from bulging upon inflation of the inflatable bladder. A rigid or semi-rigid material can be used to form the first major surface of the ventral portion, which also prevents bulging thereof after inflation of the bladder. The second major surface of the ventral portion can be formed from an elastic material capable of stretching, which allows optimal pressure transfer between the inflatable bladder and the abdomen of a subject. It will be appreciated that the straps, 18, 36, and 48 can be the same (e.g., a single strap) or different (e.g., each strap comprised of three separate straps).

Control Module

Figure 3A:
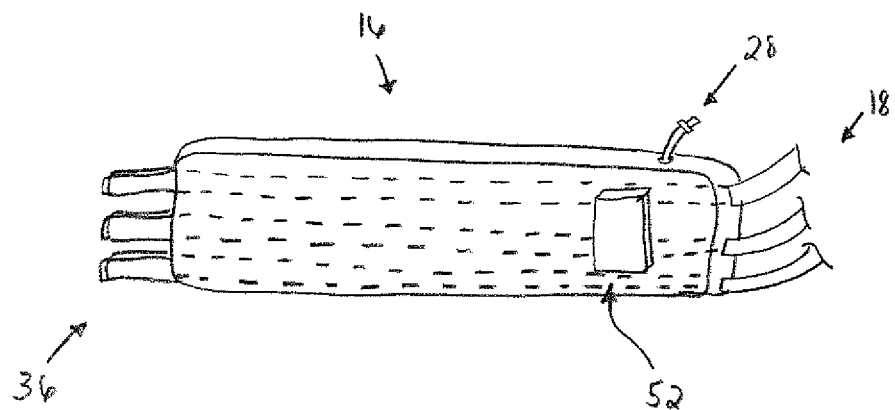
FIG. 3A is a perspective view showing an abdominal (ventral) portion of the compression device in FIG. 1 with a control module directly secured thereto.
Figure 3B:
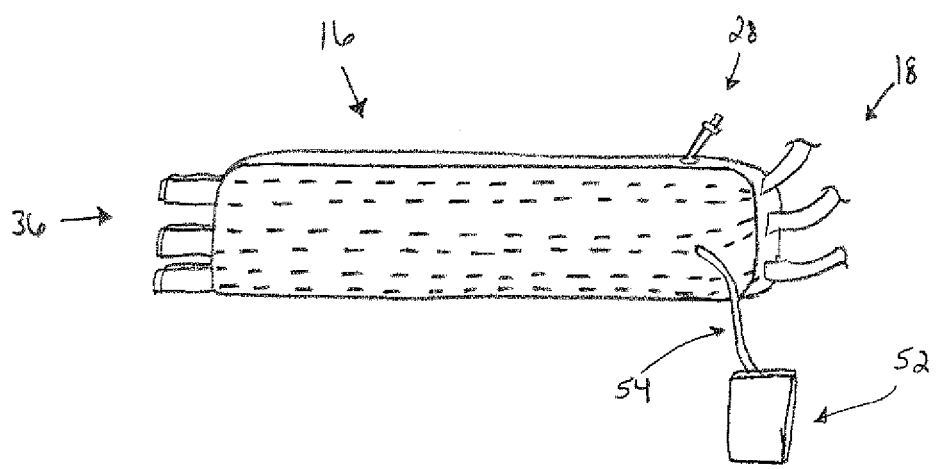
FIG. 3B is a perspective view showing the abdominal (ventral) portion of the compression device in FIG. 3A with the control module connected thereto via a cable.

Another aspect of the present disclosure can include a control module 52 (FIGS. 3A-B) secured to the compression belt 10. As discussed in more detail below, the control module 52 can house the hardware and software components needed for operation of the compression device 10. The control module 52 can be secured to compression belt 10 in a variety of ways. As shown in FIG. 3A, the control module 52 can be directly connected to the first major surface 20 of the ventral portion 16 (e.g., by an adhesive, stitches, clips, pins, etc.). Alternatively, the control module 52 can be connected to the compression belt 10 via a flexible cable 54 (FIG. 3B). In this configuration, a subject can more easily access and handle the control module 54 and, if desired, store the control module in a garment pocket, fanny pack, etc.

The control module 54 can include a housing 56 that encloses one or more hardware and/or software components, such as a pump 32 (FIG. 4), a pressure relief valve 58, and a controller that comprises a processor 60 and a memory device 62. Other hardware and/or software components that may be contained within the housing 56 are discussed below. The housing 56 can include any type of container configured to enclose the hardware and/or software component(s) of the present disclosure. In one example, the housing 56 can have a box-shaped configuration and include a hinge (not shown) that allows opposing portions of the housing to be opened and closed. When closed, an interior surface (not shown) of the housing 56 can define an interior space that is sized and dimensioned to accommodate one or more of the hardware and/or software components. Also when closed, the housing 56 can be hermetically sealed so as to prevent moisture from entering the interior space and contacting the hardware and/or software components. The housing 56 can be made of a durable and lightweight material, such as a hardened plastic (e.g., PVC). The housing 56 can also have a streamlined, ergonomic shape to facilitate ease of patient handling and to minimize its presence when the compression device 10 is worn under a garment.

In addition to the pump 32, pressure relief valve(s) 58, and the controller, additional hardware components that may be enclosed or contained within the housing 56 can include a pressure sensor 64 or pressure transducer, an accelerometer 66, a power switch (not shown), a voltage converter (not shown), a charger (not shown), a visual status indicator (e.g., LEDs) 68, and a power source (e.g., a lithium-ion rechargeable battery) (not shown), as well as other components that one skilled in the art would appreciate are needed for operation of the control module 52 (e.g., drivers, connectors, etc.). One configuration of such hardware components is shown in FIG. 4. The hardware components can be disposed on a commercially available microcontroller board (not shown), which is optionally integrated with a daughter shield (not shown). Hardware components can be in electrical communication with one another via a series of wire connectors (not shown). Control module architecture can be configured to allow multiple communication protocols (e.g., SPI, USART, I²C, etc.). In one example, information and command flow (e.g., processor controls) can be programmed and controlled via serial USART and USB interface. In some instances, the processor 60 can control the valve(s) 58 and pump 32 through standard IO ports (e.g., GPIOs). Accelerometer and pressure sensor data can be acquired via 12C Bus.

In another aspect, the pump 32 can be in fluid communication with the inflatable bladder 30. For example, flexible tubing (not shown) may be used to connect the pump 32 to the inflatable bladder 30. As discussed in more detail below, the pump 32 can be operated to inflate the bladder 30 to a pre-determined pressure (e.g., about 20-50 mm Hg) and thereby apply compressive pressure to the abdomen of a subject. In one example, the pump 32 can include a miniature diaphragm pump, such as the T2-04 pump available from Parker Hannifin, Inc. (Hollis, N.H.). The T2-04 pump is a twin head pump with a single set of ports and a double diaphragm design. The T2-04 can provide flow rates of up to 7.5 LPM, and is configured to have a low power draw.

In another aspect, the control module 52 can include one or more pressure relief valves 58. The pressure relief valve(s) 58 can be in fluid communication with the inflatable bladder 30. As discussed in more detail below, the pressure relief valve(s) 58 can be operated and controlled to decrease pressure within the inflatable bladder 30 (e.g., when a subject transitions between a standing-sitting or standing-supine posture). One example of a suitable pressure relief valve 58 can include the X-VALVE (Parker Hannifin, Inc., Hollis, N.H.), which is a miniature pneumatic solenoid valve capable of supporting a large range of pressure options (e.g., 6 psi, 30 psi and 100 psi).

In another aspect, the control module 52 can include at least one pressure sensor 64 or pressure transducer located within the housing 56. The pressure sensor(s) 64 can be configured to detect the pressure within the inflatable bladder 30, which may then be relayed to the controller. In one example, a suitable pressure sensor 64 can include an ASDX Series pressure transducer, which is commercially available from Honeywell, Inc. (Morristown, N.J.). ASDX Series pressure transducers are fully calibrated and temperature-compensated for sensor offset, sensitivity, temperature effects, and non-linearity using an on-board ASIC. ASDX Series pressure transducers can operate at low voltages, and are capable of sensing a range of pressure (e.g., from 10 psi to 100 psi).

Figure 5A:
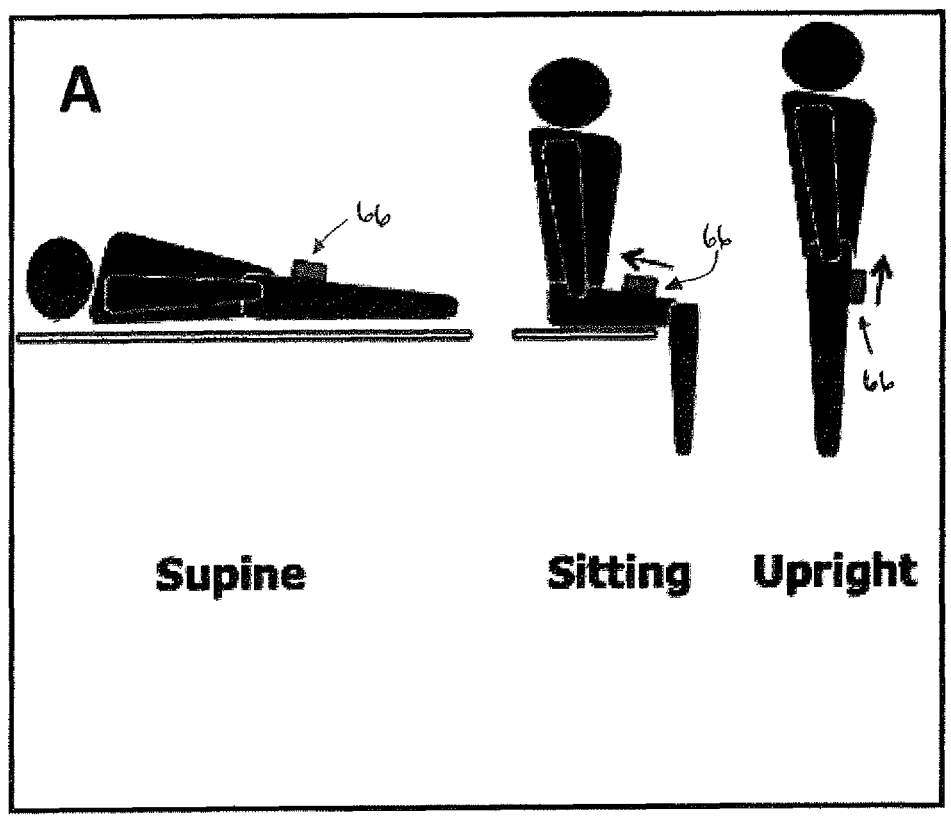
FIG. 5A is a schematic illustration showing a subject transitioning between supine, sitting, and upright postures with an accelerometer attached to a thigh of the subject.
Figure 5B:
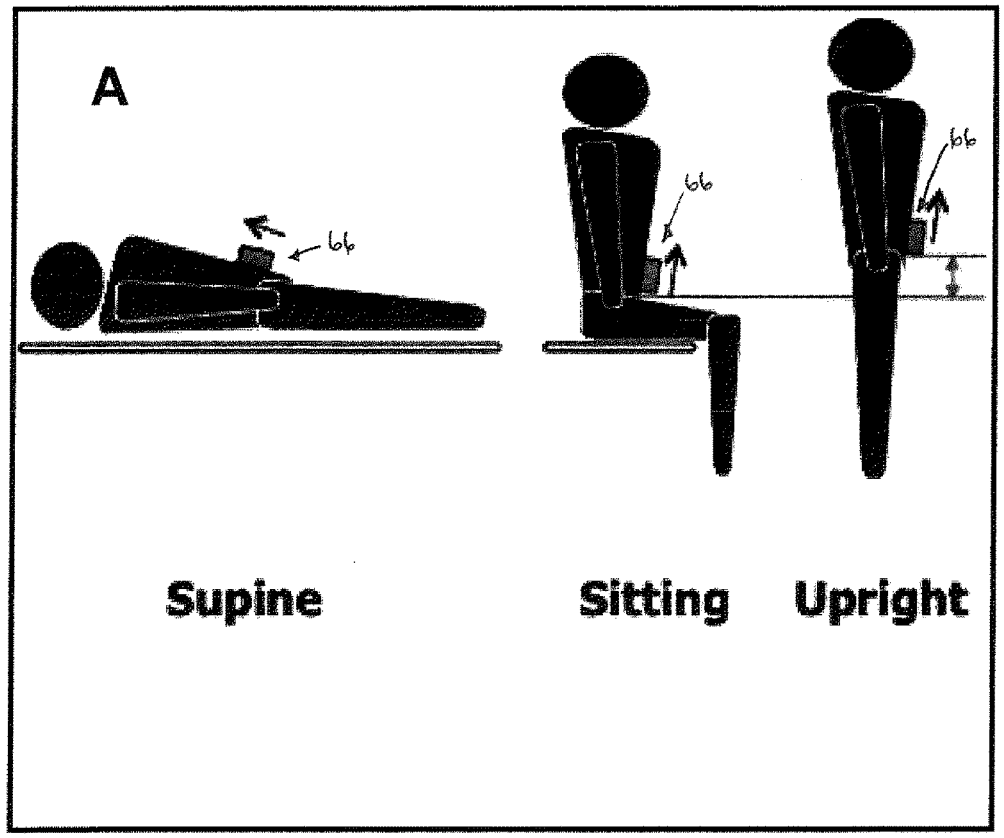
FIG. 5B is a schematic illustration showing a subject transitioning between supine, sitting, and upright postures with an accelerometer attached to the waist of the subject.

In another aspect, one or more external accelerometers 66 can be connected to the control module 52 via a direct electrical linkage (e.g., a cable or wire) or a wireless electrical linkage. Each accelerometer 66 is capable of detecting a change in the posture of a subject, which can then be relayed to the controller. The accelerometer 66 can be securely affixed to a portion of a subject's body, such as a thigh (FIG. 5A). In this configuration, the accelerometer 66 can comprise a 2-axis accelerometer capable of detecting a sitting-standing transition and/or standing-sitting transition. When fixed on a thigh, for example, a 2-axis accelerometer can sense upright posture in the x-y axis. When the accelerometer 66 is in the horizontal position, a signal indicative of the subject's posture can be relayed to the pump 32, which then triggers deflation of the inflatable bladder 30. When the subject stands up, a different signal can be sent from the accelerometer 66 to the pump 32, which is activated to inflate the inflatable bladder 30. In one example, the accelerometer 66 can include an ACTIVPAL accelerometer, which is commercially available from PAL Technologies Ltd. (Glasgow, UK).

In another aspect, one or more accelerometers 66 can be contained within the control module 52. Each accelerometer 66 is capable of detecting a change in the posture of a subject, which can then be relayed to the controller. In one example, the accelerometer 66 can comprise a 3-axis accelerometer capable of detecting motion in x-y-z planes. Advantageously, locating a 3-axis accelerometer within the control module can not only improve patient satisfaction and compliance (e.g., by removing the need to place an accelerometer 66 on the thigh of a subject), but also provide the ability to differentiate supine from seated postures.

In another aspect, the controller can include a processor 60 and a memory device 62. In some instances, the memory device 62 can include solid state memory that does not need to have its content periodically refreshed (e.g., memory which retains its state even in the event of a power loss to the memory). In one example, the memory device 62 can include non-volatile memory, such as read-only memory (ROM) (e.g., programmable ROM and erasable programmable ROM) and flash memory. The processor 60 can be configured to execute commands associated with the memory device 62. The processor 60 can include a microprocessor, for example, configured to perform arithmetic or logic operations using logic circuitry that responds to and processes commands in the memory device 62. In some instances, the processor 60 can include any conventional, general purpose single- or multi-chip microprocessor (or any one of a number of microcontrollers or other devices) that process commands. In other instances, the processor 60 can be any conventional special purpose microprocessor, such as a digital signal processor or a graphics processor. It will be appreciated that the processor 60 can additionally or optionally include conventional address lines, conventional data lines, and one or more conventional control lines.

Figure 6A:
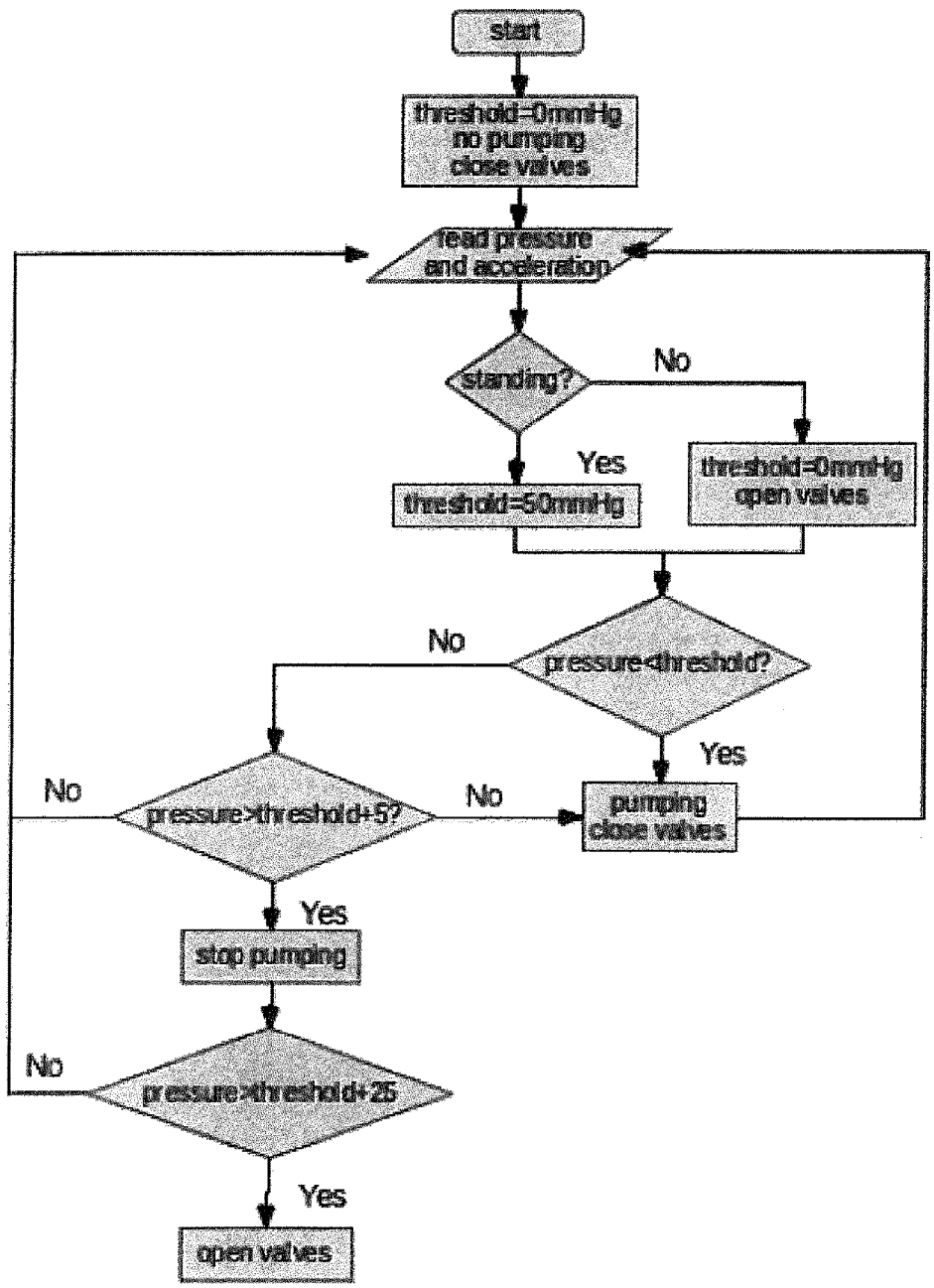
FIG. 6A is a process flow diagram illustrating one example of a pressurization/depressurization protocol for use with the accelerometer shown in FIG. 5A.

In another aspect, the memory device 62 can be programmed to include a predefined pressurization/depressurization protocol (or algorithm) for automatically adjusting the compressive pressure in response to a change in the posture of the subject (e.g., as detected by an accelerometer 66). As discussed below, the implemented pressurization/depressurization protocol can depend upon the type and/or location of the accelerometer 66. The pressurization/depressurization protocol illustrated in FIG. 6A, for example, can be implemented when the accelerometer 66 is a 2-axis accelerometer located external to the control module 52 (e.g., on the thigh of the subject). In this case, the pressurization/depressurization protocol illustrated in FIG. 6A is based on the detected acceleration of the subject's thigh. Thus, when seated, the upright vector on the accelerometer 66 is perpendicular to the gravitational vector, and the corresponding acceleration is 0 g. When standing, the upright vector on the accelerometer 66 is parallel to the gravitational vector, and the acceleration is −1 g.

Figure 6B:
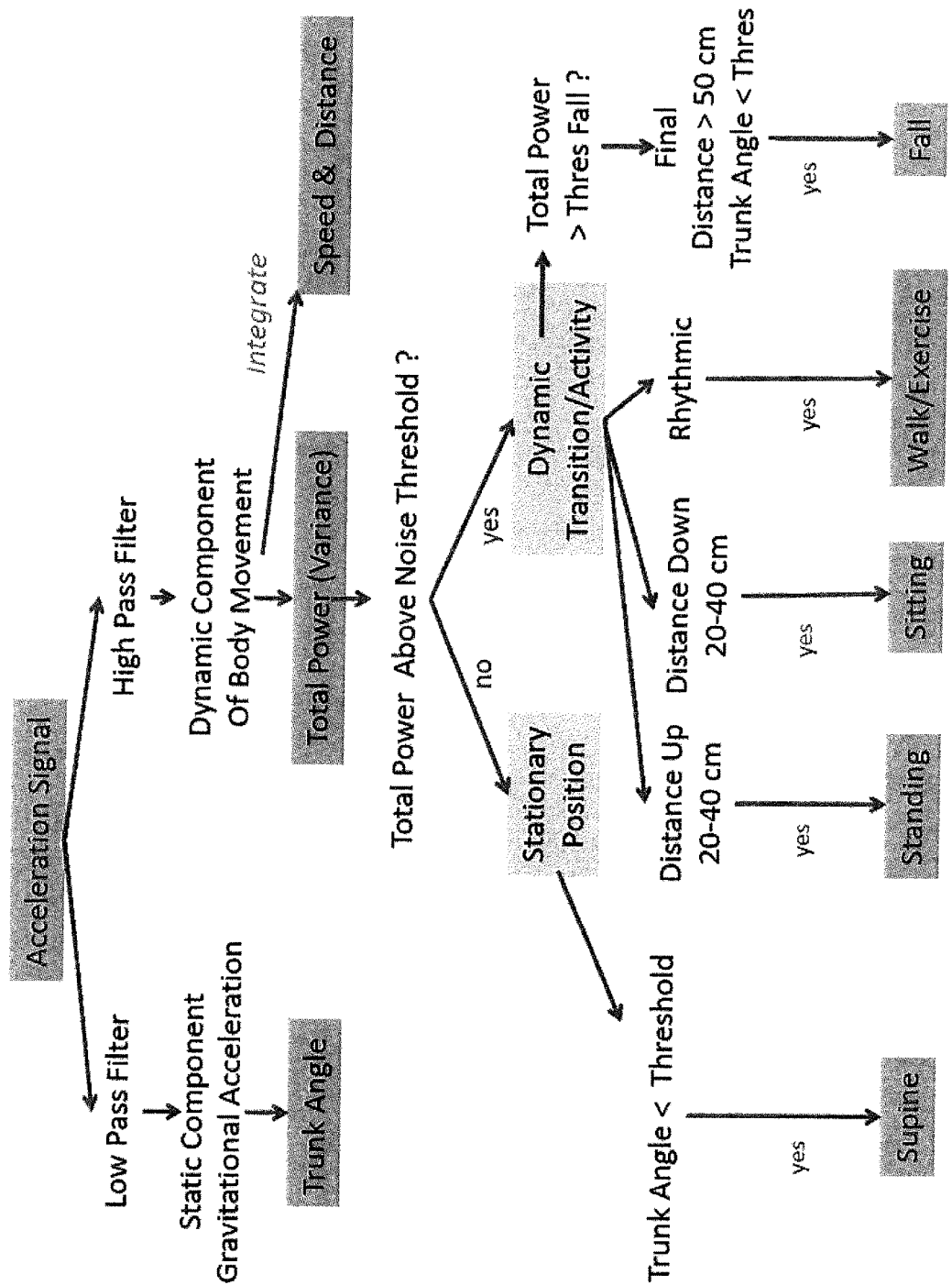
FIG. 6B is a process flow diagram illustrating one example of a pressurization/depressurization protocol for use with the accelerometer shown in FIG. 5B.

In another aspect, the pressurization/depressurization protocol (or algorithm) illustrated in FIG. 6B can be implemented when the accelerometer 66 is a 3-axis accelerometer located within the control module 52. In some instances, the pressurization/depressurization protocol shown in FIG. 6B uses multi-factorial inputs and state logic to detect supine, sitting, and standing positions. The decision tree shown in FIG. 6B can depend on trunk angle, total power in the accelerometer signal, and derived speed and distance. For example, supine posture can be detected using the orientation of the subject's torso when no movement or low amplitude movements are present. Walking can be detected by high and rhythmic activities. To determine if a subject is sitting or standing, the transition between sitting and standing can be detected. This can be done by detecting the onset of movement, integration of the accelerometer data to calculate the velocity signal, and further integration of the velocity signal to estimate the distance of vertical movement.

Systems

Figure 7:
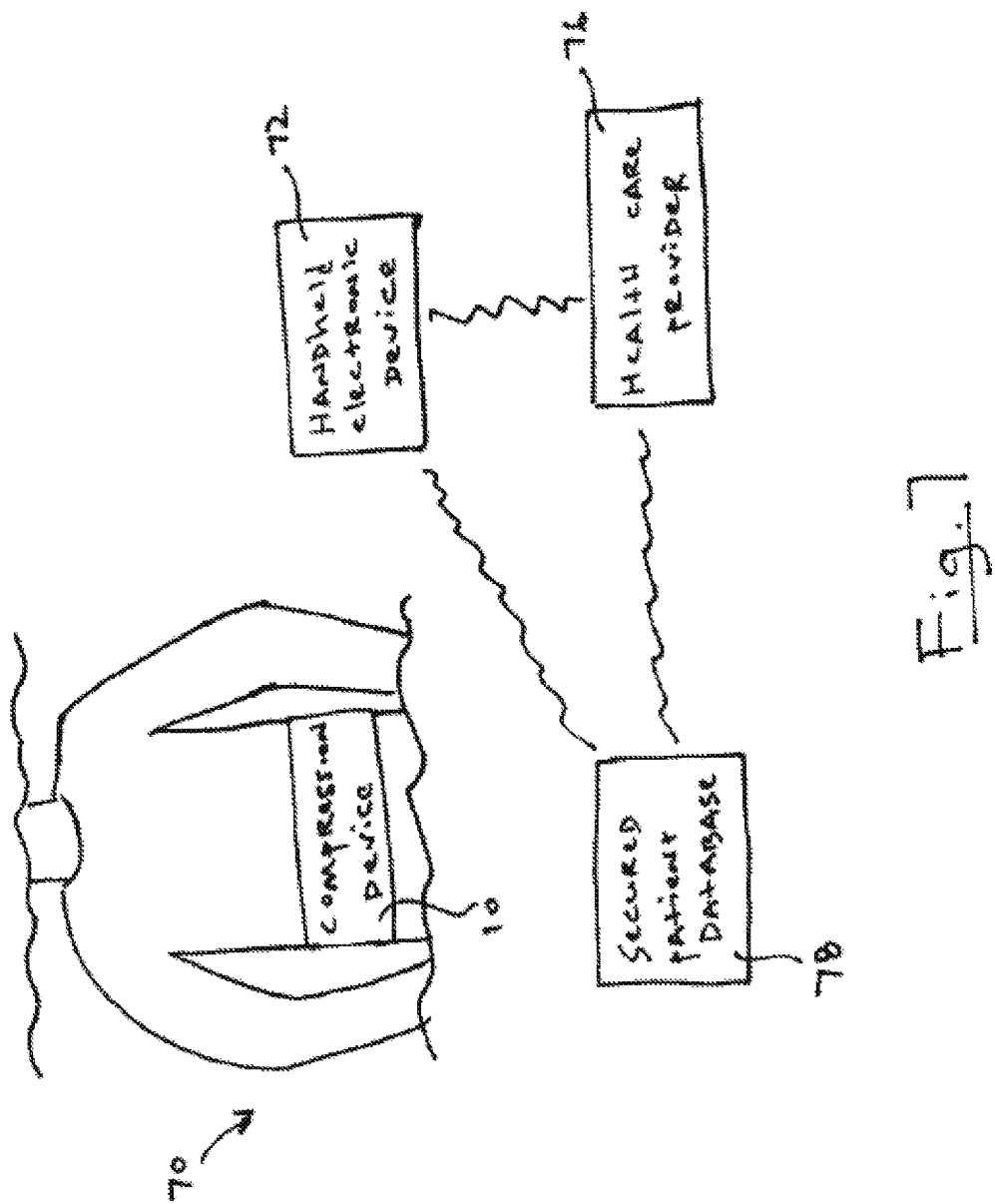
FIG. 7 is a schematic illustration showing a system for decreasing abdominal venous pooling constructed in accordance with another aspect of the present disclosure.

Another aspect of the present disclosure can include a system 70 (FIG. 7) for decreasing abdominal venous pooling in a subject. As shown in FIG. 7, the system 70 can include a compression device 10 having a controller associated therewith, and a handheld electronic device 72 in wireless communication with the controller. Other components of the system 70 are described below. In some instances, the compression device 10 can be identically or similarly constructed as the compression device shown in FIG. 1 and described above. For example, the compression device 10 of the system 70 can generally comprise an adjustable belt 12, an inflatable bladder 30 secured to the belt, and a control module 52 that is also secured to the belt. The control module 52 can further include a pump 32 in fluid communication with the inflatable bladder 30, at least one pressure relief valve 58 in fluid communication with the bladder, and a controller configured to automatically adjust a compressive pressure applied to the abdomen of a subject during operation of the system 70. As discussed below, the system 70 of the present disclosure advantageously provides a "smart" wireless compression device 10 capable of detecting posture and activity to automatically trigger inflation and deflation during upright and sitting or supine postures (respectively).

Figure 8:
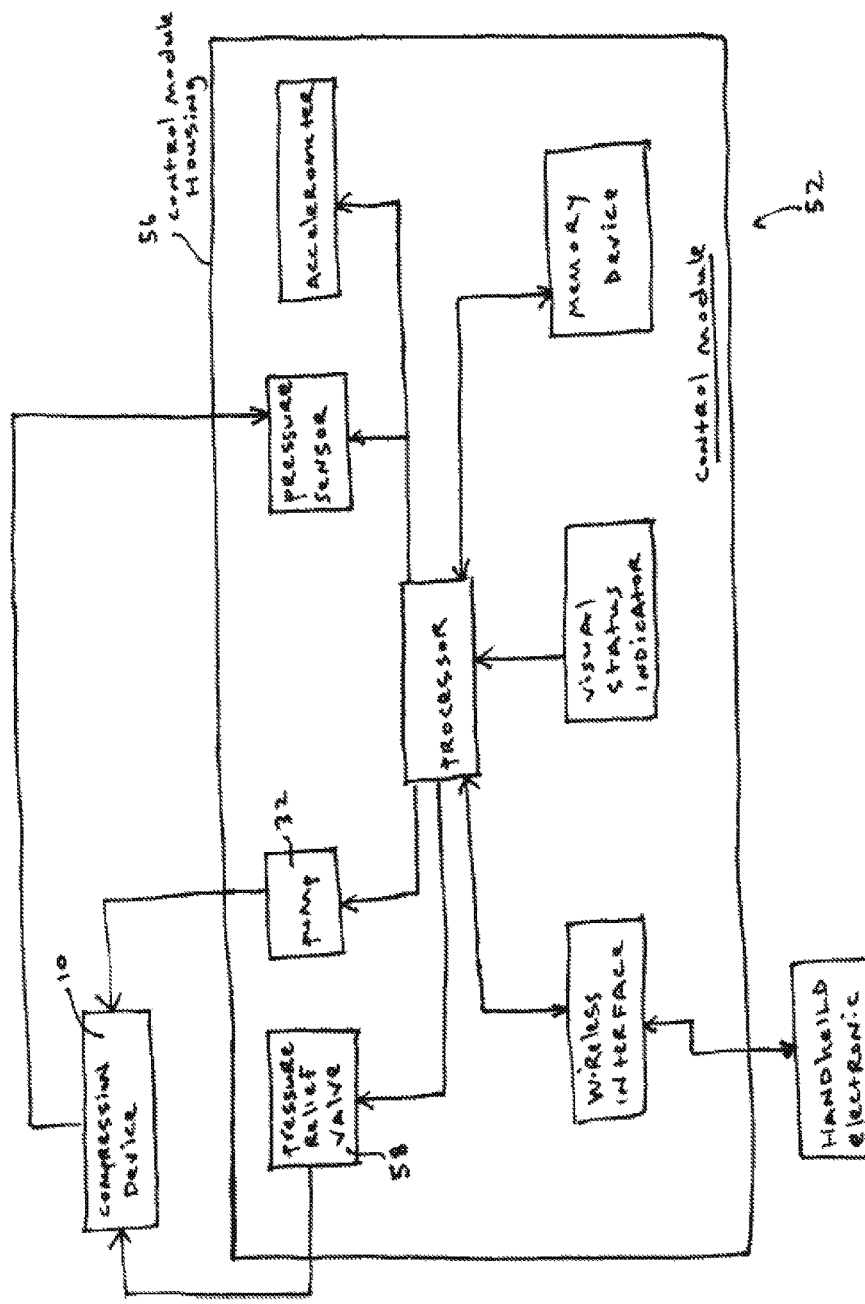
FIG. 8 is a schematic illustration showing one configuration of a control module for use with the system in FIG. 7.

As shown in FIG. 7, the handheld electronic device 72 can be in wireless communication with the compression device 10 and, in particular, the controller of the compression device. To enable wireless communication with the handheld electronic device 72, the control module 52 can be similarly or identically constructed as the control module shown in FIG. 4 and described above. For example, in addition to the hardware components described for the control module 52 in FIG. 4, the control module can further include a wireless interface 74 (FIG. 8) that enables communication between the controller and the handheld wireless device 72. In one example, the wireless interface 74 can be a Bluetooth interface. To permit activity detection (e.g., resting, walking, etc.), it will be appreciated that the system 70 can include a first accelerometer 66 located in the control module 52 (e.g., to detect posture), and one or more additional accelerometers (not shown) secured to a body part (other than the torso) of the subject (e.g., a thigh, arm, etc.). Although not shown, it will also be appreciated that the system 70 can include additional sensors capable of detecting a physiological parameter of interest. For example, the system 70 can include a sensor that provides blood pressure information to the subject and/or a health care provider 76 (FIG. 7), thereby improving control of the compressive pressure applied to the subject.

The handheld electronic device 72 can include any electronic device that is typically operated while being held in one or both hands of a subject. Cellular phones, PDAs, tablets, media players, and GPS units are examples of handheld portable electronic devices. In one example, the handheld electronic device 72 can include a GPS-enabled smartphone. In such instances, the smartphone can include an intuitive, patient-friendly interface that is: (1) speech-activated and graphic-guided; (2) capable of automatically logging activity behavior and, when needed, functioning as a notification or alert system to a health care provider 76; and (3) linked to a secured patient database 78 and/or healthcare provider expert system. For example, the smartphone can be configured to query patient status and initiate status alerts to a health care provider 76 or EMS personnel with GPS location, voice, and data communications. In some instances, the smartphone interface is configured for real-time digital signal processing, which can provide immediate alarm, feedback, and remote data provision to a healthcare provider 76. For instance, patient activity can be processed and analyzed for posture and daily pattern. If the patient falls or there is a change in the patient's behavior (e.g., the patient does not get out of bed at the usual time), the smartphone interface will notify the healthcare provider 76 (e.g., via SMS and/or Internet). The same smartphone interface can additionally or optionally be used to provide patient instructions and/or for input of personalized settings. In other instances, the secured patient database 78 can provide immediate access to current patient data and generate automated reports to optimize treatment plans, adherence to medical regimens, and aid in the management of patients with chronic medical conditions. Advantageously, the real-time wireless feedback and alarm function allows the healthcare provider 76 to manage patients more effectively, adjust individual treatment parameters (e.g., blood pressure), and reduce the risk of stroke (e.g., during supine hypertension) or falls (e.g., caused by orthostatic hypotension).

Methods

Another aspect of the present disclosure can include a method 80 (FIG. 9) for decreasing abdominal venous pooling in a subject. The method 80 can be used to treat one or a combination of conditions characterized by orthostatic intolerance. The terms "treat" or "treating" can refer to therapeutically regulating, preventing, improving, alleviating the symptoms of, reversing and/or reducing the effects of a condition characterized by orthostatic intolerance. Examples of conditions treatable by the method 80 can include, but are limited to, orthostatic hypotension, post-dialytic orthostatic hypotension, syncope, orthostatic tachycardia, delayed orthostatic hypotension, post-spaceflight orthostatic intolerance, spinal cord injury, and postural tachycardia syndrome.

Figure 9:
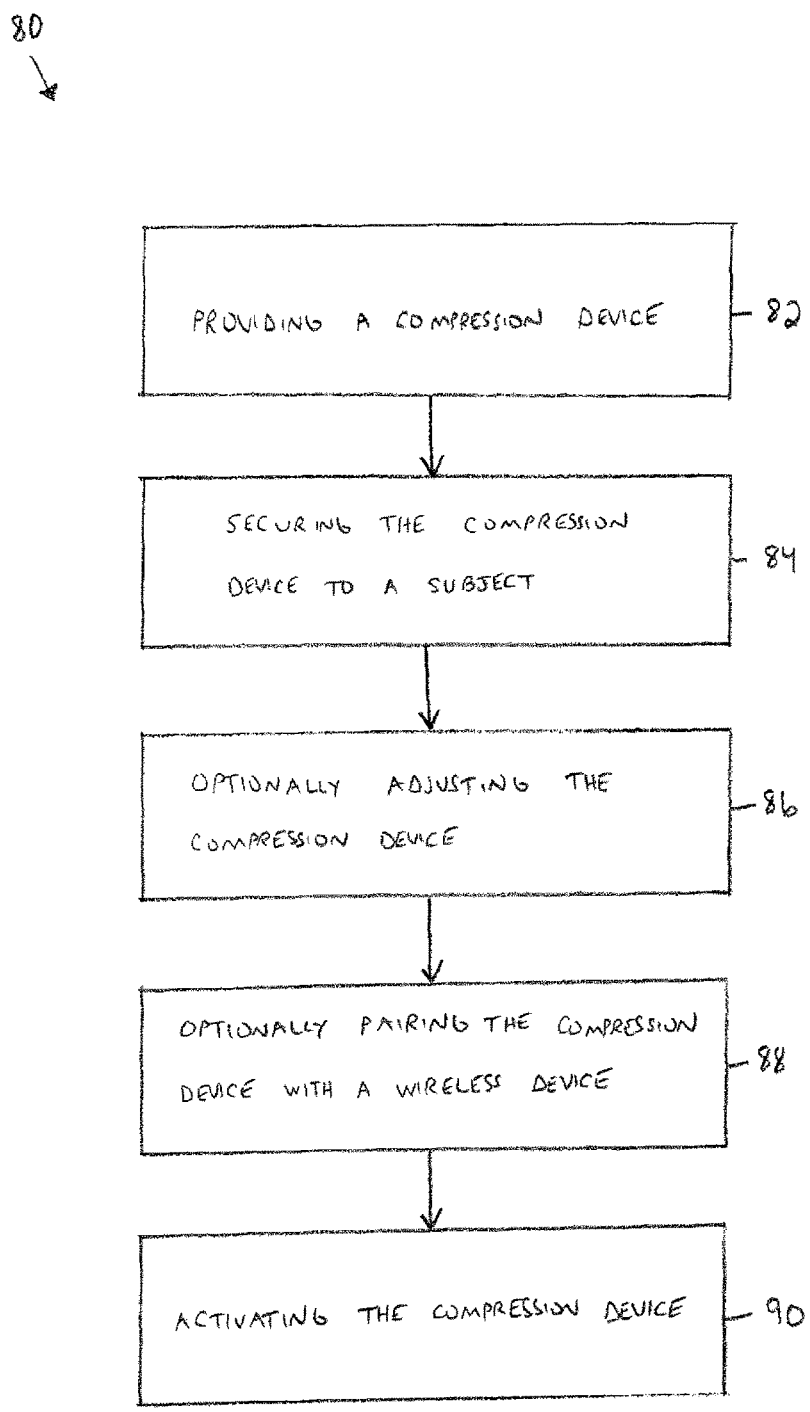
FIG. 9 is a process flow diagram illustrating a method for decreasing abdominal venous pooling in a subject according to another aspect of the present disclosure.

Generally speaking, the method 80 can comprise automatically applying a compressive pressure to the abdomen of a subject in response to a change in the posture of the subject. More particularly, and as shown in FIG. 9, the method 80 can include the following steps: providing a compression device (Step 82); securing the compression device to the subject (Step 84); optionally adjusting the compression device (Step 86); optionally pairing the compression device with a handheld wireless device (Step 88); and activating the compression device (Step 90). As discussed below, the method 80 automatically adjusts the amount of compression applied to a patient's abdomen based on the posture of the patient. This allows for normal physiologic changes in intra-abdominal pressure during routine activities, such as coughing, deep breathing, bending over, etc. Since effective compression is only applied when a patient is at an increased risk of abdominal venous pooling (e.g., when standing or transitioning to a standing position), the method 80 advantageously increases patient comfort when the patient is sitting or in a supine position.

At Step 82 of the method 80, a compression device 10 is provided. In some instances, the compression device 10 can be identically or similarly constructed as the compression device shown in FIG. 1 and described above. It will be appreciated that the particular construction of the compression device 10 can depend on a variety of factors, including the size and/or age of the subject, the general health of the subject, the familiarity of the subject with wireless technologies, the particular condition with which the subject is afflicted, etc. Once an appropriate compression device 10 has been selected, the compression device can be secured or fitted to the subject (Step 84). This can be done, for example, by first positioning the belt 12 about the waist of the subject so that the ventral and dorsal portions 16 and 14 of the belt are directly adjacent the subject's belly button and lower back, respectively. Next, the buckles comprising the attachment mechanism 34 can be snap-fit together so that the compression device 10 is circumferentially fitted around the subject's waist. The compression device 10 should be snugly positioned about the subject's waist so that movement (e.g., walking, sitting, standing, etc.) does not displace the ventral and dorsal portions 16 and 14 of the belt 12. Therefore, if needed, the fit of the belt 12 about the patient's waist can be adjusted using the attachment mechanism 34 (Step 86).

At Step 88, the compression device 10 can be optionally paired with a wireless, handheld electronic device 72, such as a GPS-enabled smartphone. In such instances, it will be appreciated that the compression device 10 can be configured as part of a system 70 (described above).

With the compression device 10 secured to the subject, the compression device can be activated at Step 90. As the subject transitions between different positions or postures over the course of a day (or night), the accelerometer(s) 66 can detect acceleration(s) (e.g., on three axises) and then send corresponding signals to the controller, which translates the signals to either "sitting", "standing" or "supine". If the detected acceleration indicates that the subject is standing, or moving from a sitting position to a standing position, the controller automatically signals the pump 32 to inflate the bladder 30 to a pre-determined pressure threshold (e.g., about 20-50 mm Hg). Consequently, compressive pressure is applied to the abdomen of the subject, which decreases venous pooling. The compressive pressure can be sustained at the pre-determined pressure throughout the transition period and/or for the time that the subject is standing. If the pressure within the inflatable bladder 30 is above the pre-determined threshold, pumping stops and the pressure relief valve(s) 58 is/are activated to release an appropriate amount of pressure. If the detected acceleration indicates that the subject is sitting, supine, or transitioning from an upright to a sitting or supine position, the controller automatically causes the pressure relief valve(s) 58 to open and thereby deflate the bladder 30. Where the compression device 10 is wirelessly paired with a handheld electronic device 72, it will be appreciated that one or more of the operations associated with the system 70 (described above) may be performed prior to, contemporaneous with, or after operation of the compression device. By automatically applying and regulating compressive pressure in subjects suffering from orthostatic intolerance, the method 80 advantageously improves upright blood pressure and reduces medical problems caused by gravity-induced venous pooling.

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The following is claimed:

1. A compression device comprising:
    an adjustable belt sized to fit circumferentially around an abdomen of a subject;
    an inflatable bladder secured to the belt, the bladder adapted to extend substantially transverse to the abdomen when the adjustable belt is circumferentially fit around the abdomen of the subject; and
    a control module secured to the belt, the control module including a housing that encloses the following:
        a pump in fluid communication with the bladder and configured to inflate the bladder to a pre-determined pressure and thereby apply a compressive pressure to the abdomen of the subject, the bladder being configured to reduce abdominal venous pooling within the internal organs of the subject when inflated to the pre-determined pressure;
        at least one pressure relief valve in fluid communication with the bladder and configured to decrease the pressure within the bladder;
        a sensor adapted to sense a change in posture of the subject; and
        a controller configured to automatically adjust the compressive pressure in response to the change in the posture of the subject sensed by the sensor, the controller being in electrical communication with the pump and the at least one pressure relief valve.

2. The device of claim 1, the bladder further including:
    a dorsal portion configured to apply compressive pressure to only the lower back of the subject; and
    a ventral portion that is oppositely disposed from the dorsal portion and configured to apply compressive pressure to only the abdomen of the subject.

3. The device of claim 1, the controller further including:
    a memory device; and
    a processor configured to execute commands in the memory device.

4. The device of claim 3, further including:
    an accelerometer located within the housing and configured to detect the change in the posture of the subject; and
    at least one pressure sensor located within the housing and configured to detect the pressure within the bladder;
    wherein each of the accelerometer and the at least one pressure sensor is in electrical communication with the controller.

5. The device of claim 4, wherein the accelerometer is a 3-axis accelerometer.

6. The device of claim 3, wherein the memory device includes a predefined pressurization/depressurization protocol for automatically adjusting the compressive pressure in response to the change in the posture of the subject.

7. The device of claim 1, wherein the controller causes the pressure in the bladder to increase to the pre-determined pressure in response to a sitting-standing transition.

8. The device of claim 1, wherein the controller causes the pressure in the bladder to decrease in response to a standing-sitting or standing-supine transition.

9. A system for decreasing abdominal venous pooling in a subject, the system comprising:
    a compression device including:
        an adjustable belt sized to fit circumferentially around the abdomen of a subject;
        an inflatable bladder secured to the belt, the bladder being adapted to extend substantially transverse to the abdomen when the adjustable belt is circumferentially fit around the abdomen of the subject; and
        a control module secured to the belt, the control module including a housing that encloses the following:
            a pump in fluid communication with the bladder and configured to inflate the bladder to a pre-determined pressure and thereby apply a compressive pressure to the abdomen of the subject, the bladder being configured to reduce abdominal venous pooling within the internal organs of the subject when inflated to the pre-determined pressure;
            at least one pressure relief valve in fluid communication with the bladder and configured to decrease the pressure within the bladder;
            a sensor adapted to sense a change in posture of the subject; and
            a controller configured to automatically adjust the compressive pressure in response to the change in the posture of the subject sensed by the sensor, the controller being in electrical communication with the pump and the at least one pressure relief valve; and
    a handheld electronic device in wireless communication with the controller.

10. The system of claim 9, wherein the controller further includes a wireless interface for communicating with the handheld electronic device.

11. The system of claim 9, wherein the handheld electronic device is a smart phone.

12. The system of claim 9, further including an accelerometer that is configured to be secured to a thigh of the subject and in wireless communication with the controller.

13. The system of claim 9, wherein the controller includes a processor for executing commands stored in a memory device, the processor:
  activating the pump to increase pressure within the bladder to the pre-determined pressure when a sitting-standing transition is detected by an accelerometer; and
  activating the at least one pressure relief valve to decrease pressure within the bladder when a standing-sitting or standing-supine transition is detected by the accelerometer;
  wherein the activating steps are based on a pressurization/depressurization protocol stored in the memory device.

14. A method for decreasing abdominal venous pooling in a subject comprising:
  providing a compression device comprising:
    an adjustable belt sized to fit circumferentially around an abdomen of a subject;
    an inflatable bladder secured to the belt, the bladder adapted to extend substantially transverse to the abdomen when the adjustable belt is circumferentially fit around the abdomen of the subject; and
    a control module secured to the belt, the control module including a housing that encloses the following:
      a pump in fluid communication with the bladder and configured to inflate the bladder to a pre-determined pressure and thereby apply a compressive pressure to the abdomen of the subject, the bladder being configured to reduce abdominal venous pooling within the internal organs of the subject when inflated to the pre-determined pressure;
      at least one pressure relief valve in fluid communication with the bladder and configured to decrease the pressure within the bladder;
      a sensor adapted to sense a change in posture of the subject; and
      a controller configured to automatically adjust the compressive pressure in response to the change in the posture of the subject sensed by the sensor, the controller being in electrical communication with the pump and the at least one pressure relief valve;
  using the compression device to automatically apply a compressive pressure to the abdomen of the subject in response to the change in the posture of the subject sensed by the sensor.

15. The method of claim 14, wherein the compressive pressure is applied to the abdomen by inflating a compressive device worn by the subject about the abdomen.

16. The method of claim 15, wherein the compressive pressure is automatically adjusted by a pump controlled by a controller.

17. The method of claim 16, wherein the controller adjusts the compressive pressure in accordance with a predefined pressurization/depressurization protocol.

18. The method of claim 17, further comprising:
  activating the pump to increase pressure within the bladder when a sitting-standing transition is detected by an accelerometer associated with the compressive device; and
  activating at least one pressure relief valve associated with the compressive device to decrease the pressure within the bladder when a standing-sitting or standing-supine transition is detected by the accelerometer.

19. The method of claim 14, wherein the subject is suffering from a condition characterized by orthostatic intolerance selected from the group consisting of orthostatic hypotension, post-dialytic orthostatic hypotension, syncope, orthostatic tachycardia, delayed orthostatic hypotension, post-spaceflight orthostatic intolerance, spinal cord injury, and postural tachycardia syndrome.

\* \* \* \* \*

UNITED STATES PATENT AND TRADEMARK OFFICE
CERTIFICATE OF CORRECTION

PATENT NO. : 10,179,083 B2
APPLICATION NO. : 14/439824
DATED : January 15, 2019
INVENTOR(S) : Franz Baudenbacher et al.

It is certified that error appears in the above-identified patent and that said Letters Patent is hereby corrected as shown below:

In the Specification

In Column 1, after Line 12 insert:
--GOVERNMENT FUNDING
This invention was made with government support under grant number TR000445 awarded by the National Institutes of Health. The government has certain rights in the invention.--

Signed and Sealed this
Nineteenth Day of November, 2019

Andrei Iancu
*Director of the United States Patent and Trademark Office*